United States Patent [19]

Merger et al.

[11] Patent Number: 4,879,406

[45] Date of Patent: Nov. 7, 1989

[54] PREPARATION OF PENTENOIC ESTERS FROM FORMYLVALERIC ESTERS

[75] Inventors: Franz Merger, Frankenthal; Juergen Frank, Schwetzingen; Uwe Vagi, Speyer; Rolf Fischer, Heidelberg, all of Fed. Rep. of Germany

[73] Assignee: BASF Aktiengesellschaft, Ludwigshafen, Fed. Rep. of Germany

[21] Appl. No.: 205,354

[22] Filed: Jun. 10, 1988

[30] Foreign Application Priority Data

Jun. 15, 1987 [DE] Fed. Rep. of Germany ....... 3719937

[51] Int. Cl.$^4$ .................... C07C 67/30; C07C 67/343
[52] U.S. Cl. .................................................. 560/211
[58] Field of Search ........................................ 560/211

[56] References Cited

U.S. PATENT DOCUMENTS

| 3,065,260 | 11/1962 | Konz | 560/211 |
| 4,039,584 | 8/1977 | Falbe et al. | 560/211 |
| 4,336,403 | 6/1982 | Merger | 560/211 |
| 4,517,400 | 5/1985 | Pesa et al. | 585/638 |

FOREIGN PATENT DOCUMENTS

| 0031100 | 6/1982 | European Pat. Off. . |
| 0125567 | 1/1986 | European Pat. Off. . |
| 0081090 | 5/1987 | European Pat. Off. . |
| 1917244 | 6/1972 | Fed. Rep. of Germany . |

OTHER PUBLICATIONS

Journal of American Chemical Society, vol. 90, (1968), pp. 94–98.
Journal of the Americal Chemical Society, vol. 90, (1968), pp. 99–107.

Primary Examiner—Paul J. Killos
Attorney, Agent, or Firm—Keil & Weinkauf

[57] ABSTRACT

Pentenoic esters are prepared by a process in which 4- and/or 3-formylvaleric esters are heated to 50°–400° C. in the presence of a catalyst which contains one or more elements of subgroup VIII of the Periodic Table.

13 Claims, No Drawings

PREPARATION OF PENTENOIC ESTERS FROM FORMYLVALERIC ESTERS

In the hydroformylation of pentenoic esters, as described in European Patent Applications Nos. 31,100 and 125,567, a mixture of isomeric 5-, 4- and 3-formylvaleric esters is obtained. For further use, however, frequently only one of the isomers is required, the other isomers being byproducts. If, for example the 5-formylvaleric ester is the desired end product, the 4- and 3-formylvaleric esters are byproducts which cannot be utilized.

J. Amer. Chem. Soc. 90 (1968), 94–98 discloses that straight-chain aldehydes can be converted in the presence of metallic palladium or platinum on a carrier to give olefins which contain one carbon atom less than the starting aldehyde. Starting from n-decanal, a mixture of 3 isomeric nonenes and 27% of nonane was obtained at 190°–195° C. in the presence of palladium on active carbon. On the other hand, cleavage of β-phenylpropionaldehyde gave 37% of ethylbenzene and only traces of styrene.

Even in the cleavage of straight-chain aldehydes in the presence of rhodium complexes, such as chlorotris(triphenylphosphine)rhodium, saturated hydrocarbons are predominantly formed. For example, when n-heptanal is used as a starting material, 86% of hexane is obtained, as stated in J. Amer. Chem. Soc. 90 (1968), 99–107.

U.S. Pat. No. 4,517,400 describes the reaction of mixtures of straight-chain and branched aldehydes over supported transition metal catalysts. In the presence of supported catalysts which contain catalytically active metals, such as platinum, palladium, rhodium, copper or zinc, virtually exclusively the straight-chain aldehydes present in the aldehyde mixture are cleaved to give olefins, while the branched aldehydes show virtually no reaction.

The cleavage of isobutyraldehyde at from 280° to 330° C. in the gas phase over supported rhodium and/or platinum catalysts has been disclosed in German Patent No. 1,917,244. Below 300° C., however, the conversion decreases substantially, so that the major part of the isobutyraldehyde used is recovered unchanged.

Since European Patent Application No. 81,090 disclosed that 4-formylcarboxylic esters undergo cyclization to 3,4-dihydro-2-pyrones at from 150° to 600° C., it was to be assumed that formylvaleric esters would be cyclized in a similar manner.

It is an object of the present invention to provide a process for the preparation of pentenoic esters from 3- and/or 4-formylvaleric esters, in which cyclization of the formylvaleric esters is avoided, pentenoic esters are obtained with high conversion and in good yield and furthermore only a small amount of saturated carboxylic esters are obtained.

We have found that this object is achieved by a process for the preparation of pentenoic esters, wherein 3- and/or 4-formylvaleric esters are treated at from 50° to 400° C. in the presence of a catalyst which contains one or more elements of subgroup VIII.

The novel process gives pentenoic esters with high conversion and high selectivity. Hydrogenation to saturated carboxylic esters is substantially avoided. Cyclization to dihydropyrones can be virtually completely eliminated.

4- and 3-formylvaleric esters derived from, preferably, alkanols of 1 to 12 carbon atoms or cycloalkanols of 5 to 8 carbon atoms are used as starting materials, individually or as a mixture. Formylvaleric esters of lower alkanols, in particular those of 1 to 6 carbon atoms, in particular methanol, are particularly preferred. Examples are methyl, ethyl, propyl, isopropyl, butyl, pentyl, hexyl, nonyl, dodecyl and cyclohexyl 4- and 3-formylvalerate. Mixtures of 3- and 4-formylvaleric esters which may furthermore contain small amounts of 5-formylvaleric esters are particularly important industrially. Typical mixtures contain, for example, from 60 to 75% by weight of 4-formylvaleric esters, from 25 to 35% by weight of 3-formylvaleric esters and up to 5% by weight of 5-formylvaleric esters.

According to the invention, the catalysts used contain one or more elements of subgroup VIII of the Periodic Table.

It is possible to use complexes of noble metals of subgroup VIII, in particular ruthenium or rhodium, as homogeneous catalysts. Ruthenium or rhodium complexes which contain halogens, such as chlorine or bromine, and phosphines or phosphites and may additionally contain carbon monoxide as a ligand are particularly suitable. Particularly preferred modifiers are tertiary organic phosphines. Preferred substituents of such phosphines are alkyl of not more than 18 carbon atoms, cycloalkyl of 5 to 12 carbon atoms, aralkyl of 7 to 10 carbon atoms or aryl of 6 to 10 carbon atoms, in particular phenyl. The radicals may be identical or different. Examples of suitable complexes are $RhCl[P(C_6H_5)_3]_3$, $Ru_2Cl_3[(P(C_6H_5)(C_2H_5)_2)_6]Cl$, $RhBr(CO)[P(C_6H_5)_3]_2$, $HRuCl(CO)[P(C_6H_5)_3]_3$ and $RhCl(CO)[P(C_6H_5)_3]_2$.

Preferably used supported catalysts are those which contain one or more of the elements palladium, platinum, ruthenium, rhodium, osmium, iridium, iron, cobalt and nickel, in particular noble metals. Other advantageous supported catalysts are those which contain two or more noble metals selected from the group consisting of ruthenium, rhodium, palladium, platinum, iridium and osmium. Other preferred supported catalysts contain one or more of the abovementioned noble metals of subgroup VIII of the Periodic Table and in addition one or more metals selected from the group consisting of iron, cobalt and nickel.

The supported catalysts advantageously contain active metals of subgroup VIII of the Periodic Table in an amount of from 0.01 to 10, preferably from 0.05 to 5, in particular from 0.05 to 1, % by weight, based on the sum of the carrier and catalytically active metals, calculated as metal. Advantageous carriers are alumina, silica, titanium dioxide, zinc oxide, lanthanum oxide, zirconium dioxide, barium sulfate, aluminum silicates and mixtures of these.

Particularly advantageous supported catalysts additionally contain one or more elements of subgroups I to VII and/or rare earth elements, for example zinc, copper, silver, lanthanum, titanium, vanadium, chromium, molybdenum, tungsten, manganese, rhenium, cerium, neodymium or praseodymium, advantageously in an amount of from 0.05 to 2% by weight, calculated as metal and based on the total weight of the catalyst (carrier and catalytically active metals).

For example, impregnated catalysts in which the catalytically active metals are concentrated at the surface of the carrier have proven useful. Catalysts of this type are prepared in a conventional manner by impregnating preshaped carriers, such as pellets, spheres or extrudates, with an aqueous solution of the metal salts which are converted into their oxides on heating, e.g. the nitrates, and the products can then be dried, calcined and used directly or if necessary after reduction with hydrogen or other reducing agents.

The preferably used supported catalysts have high activity over a prolonged period. Spent catalysts can be regenerated by treatment with a gas containing molecular oxygen, e.g. air, at from 350° to 500° C., followed by reduction.

In the cleavage of the formylvaleric esters, a temperature of from 50° to 400° C., advantageously from 60° to 350° C., preferably from 100° to 280° C., in particular from 120° to 200° C., is maintained. In general, the cleavage is carried out under atmospheric pressure although it is also possible to use reduced or superatmospheric pressure, advantageously from 10 mbar to 20 bar. In general, a space velocity of from 0.01 to 40, preferably from 0.1 to 20, kg of formylvaleric ester per kg of catalyst per hour is maintained.

It may be advantageous to carry out the cleavage of the formylvaleric esters in the presence of a diluent. Suitable diluents are water, alcohols, such as methanol, ethanol, butanol or cyclohexanol, ethers, such as dioxane or tetrahydrofuran, chlorohydrocarbons, such as methylene chloride, chloroform or 1,2-dichloromethane, aliphatic, cycloaliphatic or aromatic hydrocarbons, such as benzene, toluene, cyclohexane or paraffins, and esters, such as acetates or propionates. It is advantageous to use the alcohol corresponding to the alcohol of the formylvaleric esters. Thus, the educt and product have sufficiently different boiling points and can therefore be readily separated by distillation. It has proven useful for the molar ratio of formylvaleric esters to diluents to be from 1:0.1 to 1:50, in particular from 1:0.5 to 1:20. Particularly preferred diluents are water and alkanols of 1 to 6 carbon atoms or mixtures of these, in particular methanol.

The cleavage is advantageously carried out in the presence of molecular oxygen or of a gas which contains molecular oxygen as well as an inert gas, such as nitrogen, carbon dioxide, argon or steam. A molar ratio of formylvaleric ester to molecular oxygen of from 1:0.05 to 1:3, in particular from 1:0.2 to 1:1.5, e.g. from 1:0.5 to 1:1.25, is preferably used. This increases the catalyst life and in particular the yield of pentenoic esters. The concomitant use of molecular oxygen was not indicated, since it was known from European Patent 131,860 that methyl 5-formylvalerate is oxidized to monomethyl adipate in a yield of 96% by molecular oxygen at as low as 50° C., and it was therefore to be expected that 4- and 3-formylvaleric esters would be oxidized in a similar manner to give monomethyl 2-methylglutarate and monomethyl 3-ethylsuccinate.

The reaction can be carried out batchwise or continuously, using a fixed-bed catalyst, for example by the liquid phase or trickle-bed procedure, in the liquid or gas phase, or as a fluidized-bed reaction with the fluidized catalyst moving upward and downward, in the gas phase, or in the liquid phase with soluble catalysts or suspended supported catalysts.

In a preferred embodiment in the liqiuid phase, for example, formylvaleric esters and, if required, diluents together with an oxygen-containing gas are passed, at below the boiling point of the formylvaleric ester, over a solid catalyst, or are heated in the presence of a suspended, solid catalyst or of a dissolved homogeneous catalyst. After the catalysts have been separated off, the liquid reaction product is separated by distillation into pentenoic esters and, where relevant, diluents and unconverted formylvaleric esters, which can be recycled.

In a preferred embodiment of the novel process in the gas phase, for example, a mixture of formylvaleric esters and, if required, diluents is vaporized and then passed together with air and, advantageously, also a carrier gas, such as nitrogen, carbon dioxide or argon, at the abovementioned temperature and in gaseous form, into a fixed-bed or fluidized catalyst. The reacted mixture is condensed and then separated by fractional distillation. Unconverted formylvaleric esters are advantageously recycled. The resulting mixture of 4-, 3- and 2-pentenoic esters can be used directly for hydroformylation to give 5-formylvaleric esters.

The Examples which follow illustrate the process according to the invention.

EXAMPLE 1

10 ml/hour of a mixture of methyl 4-formylvalerate (4-FVSE), tetrahydrofuran and water (23% by weight of 4-FVSE, 10% by weight of water, remainder methanol) were pumped into an evaporator and passed from there, together with 3 l/hour of nitrogen, at 250° C. over 10 g of catalyst. The gaseous reacted mixtures were condensed in cold traps, weighed, and analyzed by gas chromatography. Table 1 shows the composition of the reacted mixtures after an experimental time of 4 hours in each case (PSE=methyl pentenoate).

TABLE 1

| No. | Catalyst | PSE[1] mol % | Conversion % | PSE select. % |
|---|---|---|---|---|
| 1 | 1% Pt on SiO$_2$ | 32 | 51 | 63 |
| 2 | 0.5% Ru/0.5% Rh on SiO$_2$ | 61 | 88 | 69 |
| 3 | 0.5% Rh/0.5% Pt on SiO$_2$ | 55 | 96 | 57 |
| 4 | 0.5% Rh/0.5% Ru/0.5% Pt on SiO$_2$ | 71 | 99 | 71 |

[1]Mixture of isomeric methyl pentenoates

COMPARATIVE EXAMPLE 1

When Example 1 was repeated using 10 g of SiO$_2$, without the addition of platinum, as the catalyst, after a reaction time of 4 hours the reacted mixture contained 70.8% of 4-FVSE and 25.9% of 5-methyl-3,4-dihydro-2-pyrone, according to analysis by gas chromatography (% by area).

EXAMPLE 2

10 ml/hour of a mixture of 4-FVSE, methanol and water (30% by weight of 4-FVSE, 10% by weight of water, remainder methanol) were pumped into an evaporator and passed from there, together with 3 l/hour of air, at 250° C. over 10 g of catalyst. The gaseous reacted mixtures were condensed in cold traps, weighed, and analyzed by gas chromatography. The catalyst used and the results obtained are shown in Table 2.

TABLE 2

| No. | Catalyst | PSE mol % | Conversion % | PSE select. % |
|---|---|---|---|---|
| 1 | 1% Pt on SiO$_2$ | 26 | 52 | 49 |
| 2 | 0.5% Ru/0.9% Rh on SiO$_2$ | 67 | 96 | 70 |
| 3 | 0.5% Rh/0.5% Pt on SiO$_2$ | 44 | 99 | 44 |
| 4 | 0.5% Rh/0.5% Ru/0.5% Pt on SiO$_2$ | 72 | 94 | 77 |
| 5 | 0.5% Rh/0.5% Ru/0.5% Ag on SiO$_2$ | 58 | 98 | 59 |

TABLE 2-continued

| No. | Catalyst | PSE mol % | Conversion % | PSE select. % |
|---|---|---|---|---|
| 6 | 0.5% Rh/0.5% Ru/0.5% Fe on SiO$_2$ | 52 | 91 | 57 |
| 7 | 0.5% Rh/0.5% Ru/0.5% Cr on SiO$_2$ | 35 | 98 | 36 |

EXAMPLE 3

10 ml/hour of a mixture of 4-FVSE, methanol and water (30% by weight of 4-FVSE, 10% by weight of water, remainder methanol) were pumped into an evaporator and passed from there, together with 3 l/hour of air, at 250° C. over 10 g of catalyst (0.5% of Ru, 0.5% of Rh and 0.5% of Pt on silica). The gaseous reacted mixtures were condensed in cold traps, weighed, and analyzed by gas chromatography. Table 3 shows the composition of the reacted mixtures after the relevant experimental time.

TABLE 3

| No. | Experimental time h | PSE mol % | Conversion % | PSE selectivity % |
|---|---|---|---|---|
| 1 | 10 | 60 | 99 | 67 |
| 2 | 34 | 66 | 99 | 67 |
| 3 | 58 | 70 | 95 | 74 |
| 4 | 130 | 72 | 94 | 77 |
| 5 | 198 | 64 | 84 | 76 |
| 6 | 300 | 65 | 84 | 77 |

After an experimental time of 300 hours, the combined reacted mixtures were subjected to fractional distillation. 428 g of a methyl pentenoate/methyl valerate mixture (80% of pentenoic esters comprising 25% of methyl 4-trans-pentenoate, 70% of methyl 3-trans-pentenoate and 5% of methyl 2-trans-pentenoate/20% of valeric ester) were obtained, the yield of pentenoic esters being 60% of theory and that of valeric ester being 15% of theory.

EXAMPLE 4

45 ml/hour of a 37.5% strength by weight 3-FVSE solution in methanol were pumped into an evaporator and passed from there, together with 12 l/hour of air, at 250° C. over 30 g of catalyst (0.5% of Ru and 0.85% of Rh on silica). The gaseous reacted mixtures were condensed in cold traps over an experimental time of 6 hours, weighed, and analyzed by gas chromatography. The result was as follows:

| PSE [mol %] | VSE [mol %] | Conversion [%] | PSE selectivity [%] |
|---|---|---|---|
| 60 | 15 | 85 | 71 |

EXAMPLE 5

45 ml/hour of a 37.5% strength by weight FVSE solution in methanol (63% of 4-FVSE and 32% of FVSE) were pumped into an evaporator and passed from there, together with 12 l/hour of air, at 250° C. over 30 g of catalyst (0.5% of Ru and 0.85% of Rh on silica). The gaseous reacted mixtures were condensed in cold traps over an experimental time of 100 hours, weighed, and analyzed by gas chromatography. The result was as follows:

| PSE [mol %] | VSE [mol %] | Conversion [%] | PSE selectivity [%] |
|---|---|---|---|
| 62 | 13 | 82 | 76 |

EXAMPLE 6

In a 1 reaction flask having a distillation apparatus for the reaction products, 150 g of high boiling aldolization products of methyl formylvalerates were initially taken as solvents, the said aldolization products containing 10 g of chlorocarbonylbis-(triphenylphosphine)rhodium complex (ClRh(CO)(PPh$_3$)$_2$).

50 g/hour of a mixture of formylvaleric esters (69% of 4-FVSE, 29% of 3-FVSE and 2% of 5-FVSE) were added to this catalyst solution at from 230° to 240° C.

The reaction products were distilled off continuously. 47 g of distillate were obtained per hour and were shown by gas chromatographic analysis to contain 10.1% by weight of methyl valerate and 50.2% by weight of methyl pentenoates (isomer mixture). This corresponds to a yield of 60%, based on formylvaleric esters used, of methyl pentenoates.

EXAMPLE 7

30 g/hour of 96.6% pure methyl 4-formylvalerate, together with 24 l/h of N$_2$ and 6 l/h of air, were passed over 20 g of catalyst (0.75% of Ni and 0.25% of Pd on silica) at 130° C. 186.1 g of starting material gave 162 g of reacted mixture. Distillation of the said mixture gave 66.8 g of a product which had a boiling range of from 93° to 145° C. and consisted of 82% of PSE isomers. The bottom product of the distillation amounted to 93 g and contained 77.7% of FVSE and 9.6% of PSE. This gave a conversion of 62% and a selectivity of 77%.

EXAMPLES 8 TO 18

Commercial catalyst carriers were impregnated with a metal salt solution containing the calculated amount of metal ions until saturation was reached, this taking 3 hours. Thereafter, drying was carried out under reduced pressure, after which calcination was effected at 300°-400° C. under nitrogen. The catalysts were then used for the reactions without further modification.

30 g/hour of methyl 4-formylvalerate and 30 l/hour of a gas having the stated composition were passed over 10 g of catalyst at the relevant temperature. The condensed liquid reacted mixture was analyzed by gas chromatography, and the conversion and selectivity calculated from the analytical result. The details are shown in table 4.

TABLE 4

| Example | Catalyst | Gas N$_2$/air [parts by vol.] | Temp. [°C.] | PSE [% by wt.] | Conversion [%] | Select. of PSE [%] |
|---|---|---|---|---|---|---|
| 8 | 0.25% of Pd SiO$_2$ 0.75% of Ni | 4/1 | 130 | 76 | 96 | 76 |
| 9 | 0.75% of Pd SiO$_2$ 0.04% of Mn | 2/3 | 180 | 75 | 87 | 90 |
| 10 | 0.75% of Pd SiO$_2$ 0.25% of Ag | 4/1 | 180 | 47 | 79 | 55 |
| 11 | 0.75% of Pd SiO$_2$ 0.1% of Re | 3/2 | 180 | 73 | 86 | 91 |
| 12 | 0.75% of Pd | 4/1 | 180 | 46 | 74 | 70 |

TABLE 4-continued

| Example | Catalyst | Gas N$_2$/air [parts by vol.] | Temp. [°C.] | PSE [% by wt.] | Conversion [%] | Select. of PSE [%] |
|---|---|---|---|---|---|---|
| 13 | SiO$_2$ 0.1% V 0.75% of Pd | 3/2 | 180 | 72 | 89 | 85 |
| 14 | SiO$_2$ 0.1% of Ce 0.5% of Pd | 4/1 | 150 | 6 | 34 | 22 |
| 15 | SiO$_2$ 0.5% of Ru 0.75% of Pd | 3/2 | 180 | 70 | 86 | 89 |
| 16 | SiO$_2$ 0.1% of Zn 0.75% of Pd | 4/1 | 180 | 11 | 26 | 51 |
| 17 | ZrO$_2$ 0.25% of Ag 0.75% of Pd | 4/1 | 180 | 46 | 62 | 76 |
| 18 | TiO$_2$ 0.25% of Ag 1.1% of Pd BaOS$_4$ | 4/1 | 190 | 17 | 25 | 81 |

COMPARATIVE EXAMPLE 2

In a bubble column containing 217 g of methyl 4-formylvalerate, at 50° C., 5 liters/hour of oxygen were passed in from below and 40 liters/hour of nitrogen were passed in above the liquid phase. After a reaction time of 7 hours, the column was flushed with nitrogen. Fractional distillation of the reacted mixture gave 194 g of 5-methyl 2-methylglutarate (81% of theory).

We claim:

1. A process for the preparation of a pentenoic ester which comprises: heating a 3- and/or 4-formylvaleric ester to 50°–400° C. in the presence of a catalyst which contains one or more elements of subgroup VIII of the Periodic Table.

2. The process of claim 1, wherein methyl 3-formylvalerate and/or methyl 4-formylvalerate are used as the starting material.

3. The process of in claim 1, wherein a supported catalyst is used which contains from 0.01 to 10% by weight, calculated as metal and based on the sum of the carrier and active metals, of one or more metals of subgroup VIII of the Periodic Table is used.

4. The process of in claim 1, wherein the catalyst contains two or more metals selected from the group consisting of ruthenium, rhodium, palladium, platinum, iridium and osmium.

5. The process of in claim 1, wherein the catalyst contains one or more noble metals of subgroup VIII of the Periodic Table and in addition one or more metals selected from the group consisting of iron, cobalt and nickel.

6. The process of claim 1, wherein the catalyst additionally contains one or more elements of subgroups I to VII of the Periodic Table.

7. The process of in claim 1, wherein the catalyst used is a complex of ruthenium or rhodium.

8. The process as claimed in claim 1, wherein a temperature of from 60° to 350° C. is maintained.

9. The process of in claim 1, wherein molecular oxygen or a gas containing molecular oxygen is concomitantly used.

10. The process of in claim 1, wherein a molar ratio of 3- and/or 4-formylvaleric esters to molecular oxygen of from 1:0.5 to 1:3 is maintained.

11. The process of in claim 1, wherein a diluent is present.

12. The process of in claim 1, wherein the diluent used is an alcohol which corresponds to the alcohol of the formyl esters.

13. The process of in claim 1, wherein a molar ratio of formylvaleric esters to diluent of from 1:0.1 to 1:50 is maintained.

* * * * *

UNITED STATES PATENT AND TRADEMARK OFFICE
CERTIFICATE OF CORRECTION

PATENT NO. : 4,879,406

DATED : Nov. 7, 1989

INVENTOR(S) : Franz MERGER, Juergen FRANK, Uwe VAGT and Rolf FISCHER

It is certified that error appears in the above-identified patent and that said Letters Patent is hereby corrected as shown below:

Title page:

INVENTORS:

"Uwe Vagi" should read "Uwe Vagt"

IN THE CLAIMS:

Claims 3-7 and 9-13, line 1, "in" should be deleted.

Claim 3, line 5, "is used" should be deleted.

Claim 8, line 1, "as claimed in" should read "of"

Signed and Sealed this

Eighth Day of January, 1991

Attest:

HARRY F. MANBECK, JR.

Attesting Officer   Commissioner of Patents and Trademarks